(12) United States Patent
Hong

(10) Patent No.: US 9,956,265 B2
(45) Date of Patent: May 1, 2018

(54) COMPOSITION FOR AIDING SURGICAL PROCEDURES FOR TREATING ISCHEMIC VASCULAR DISEASES

(75) Inventor: Ji Man Hong, Gyeonggi-do (KR)

(73) Assignee: AJOU UNIVERSITY INDUSTRY-ACADEMIC COOPERATION FOUNDATION (KR)

( * ) Notice: Subject to any disclaimer, the term of this patent is extended or adjusted under 35 U.S.C. 154(b) by 62 days.

(21) Appl. No.: 14/113,762

(22) PCT Filed: Apr. 26, 2012

(86) PCT No.: PCT/KR2012/003260
§ 371 (c)(1),
(2), (4) Date: Oct. 24, 2013

(87) PCT Pub. No.: WO2012/148200
PCT Pub. Date: Nov. 1, 2012

(65) Prior Publication Data
US 2014/0045748 A1    Feb. 13, 2014

(30) Foreign Application Priority Data

Apr. 26, 2011   (KR) .................. 10-2011-0039219
Apr. 26, 2012   (KR) .................. 10-2012-0043799

(51) Int. Cl.
*A61K 38/18*        (2006.01)
*A61M 1/00*         (2006.01)

(52) U.S. Cl.
CPC .......... *A61K 38/1816* (2013.01); *A61M 1/00* (2013.01)

(58) Field of Classification Search
None
See application file for complete search history.

(56) References Cited

U.S. PATENT DOCUMENTS

| | | | | |
|---|---|---|---|---|
| 6,379,363 B1* | 4/2002 | Herrington | .......... | A61B 17/688 606/104 |
| 2002/0086816 A1* | 7/2002 | Brines | ................ | A61K 38/1816 514/7.7 |
| 2003/0104988 A1* | 6/2003 | Brines et al. | ...................... | 514/8 |
| 2007/0298031 A1 | 12/2007 | Brines et al. | | |
| 2008/0031850 A1 | 2/2008 | Bader | | |
| 2009/0258821 A1* | 10/2009 | Cerami et al. | ...................... | 514/8 |
| 2010/0247452 A1 | 9/2010 | Bahlmann et al. | | |

FOREIGN PATENT DOCUMENTS

| | | |
|---|---|---|
| JP | 2010-265301 | 11/2010 |
| KR | 10-2010-0077033 | 7/2010 |
| WO | 2000/35475 | 6/2000 |

OTHER PUBLICATIONS

Ommaya, A. Implantable Devices for Chronic Access and Drug Delivery to the Central Nervous System. Cancer Drug Delivery. vol. 1, No. 2, pp. 169-179 (1984).*
Endo et al. Cranial burr hole for revascularization in moyamoya disease. Journal of Neurosurgery vol. 71:180-185 (1989).*
Katayama et al. Moyamoya disease associated with persistent primitive hypoglossal artery: report of a case. Pediatric neurosurgery, Abstract. vol. 35, No. pages 262-265 (Nov. 2001).*
Matsuda et al. Moyamoya disease associated with hemophilia A. Case report. Pediatric neurosurgery, Abstract. vol. 36, No. 3, pp. 157-160 (Mar. 2002).*
Ko et al. "Surgical Results of Multiple Burr Hole Operation in Adult Moyamoya Disease". 2004, J. Korean Neurosurg Soc. vol. 35: 17-22.
International Search Report issued for International Application No. PCT/KR12/003260, dated Nov. 23, 2012.

* cited by examiner

*Primary Examiner* — Elizabeth C. Kemmerer
*Assistant Examiner* — Regina M DeBerry
(74) *Attorney, Agent, or Firm* — Riverside Law LLP

(57) ABSTRACT

The present invention relates to a composition comprising erythropoietin (EPO) as an active ingredient for aiding surgical procedures for treating ischemic vascular diseases. The present invention also relates to a method for treating ischemic vascular diseases using a combination of the composition and the invasive procedure for sufficient disruption of the physical barriers for new neovascularization. The composition for aiding surgical or invasive procedures according to the present invention would be beneficial for the success rate and safety issue of a variety of surgical procedures such as minimally invasive operations performed on a patient suffering from a variety of cerebral ischemic vascular diseases including ischemic stroke and moyamoya disease, and can be widely used in the treatment of a variety of ischemic vasculopathies in cardiac or peripheral artery system.

4 Claims, 26 Drawing Sheets

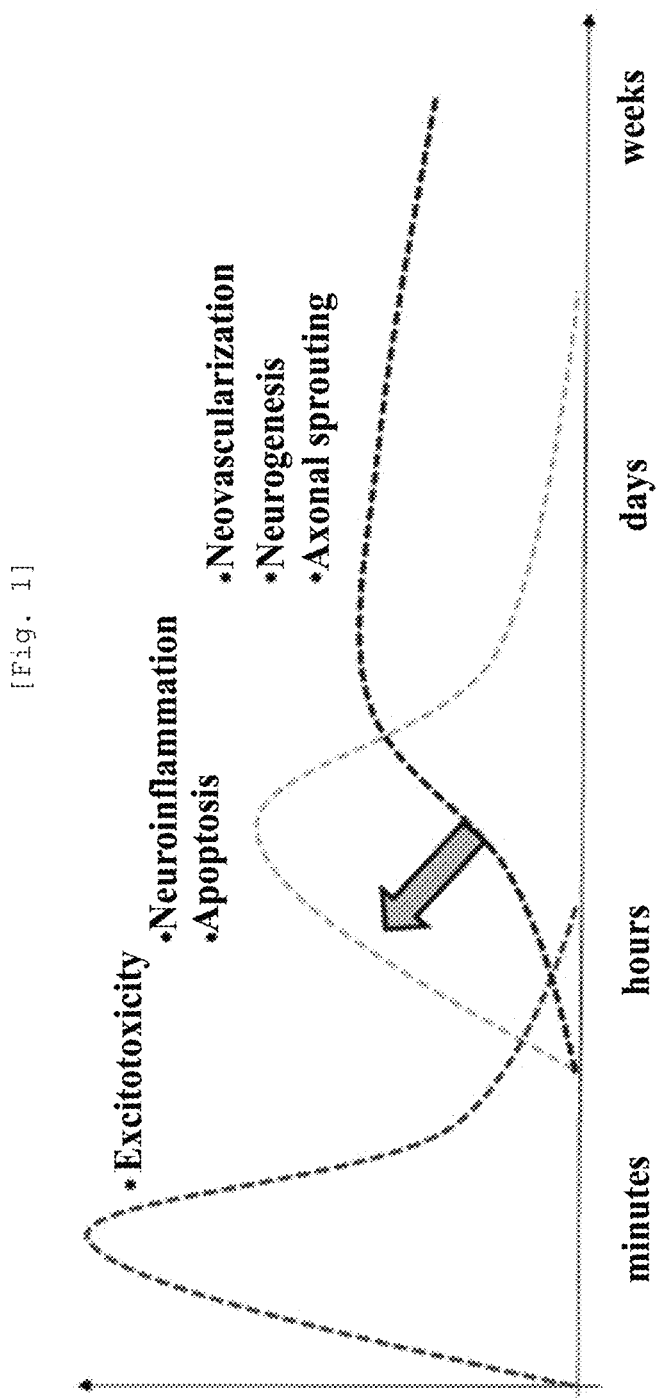

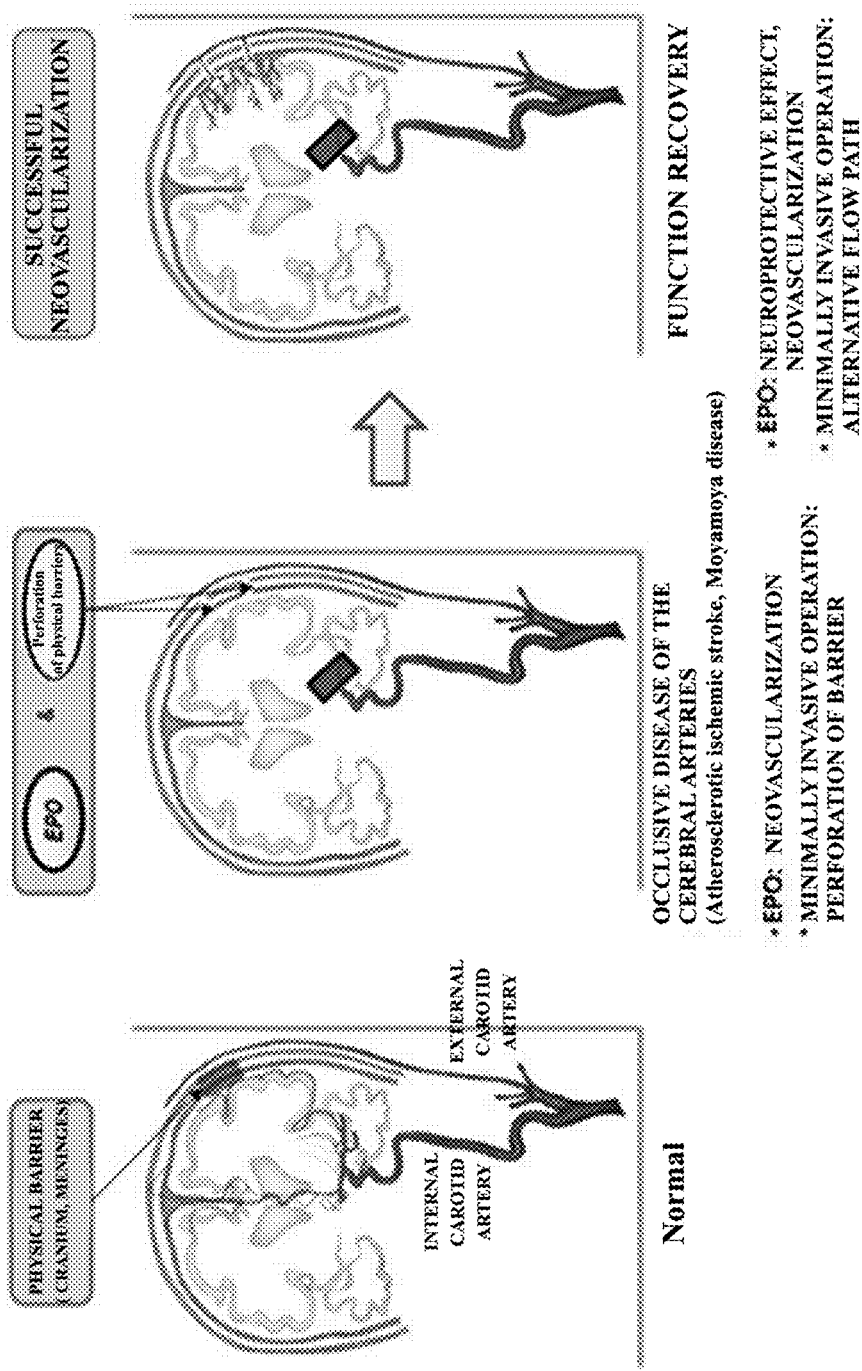

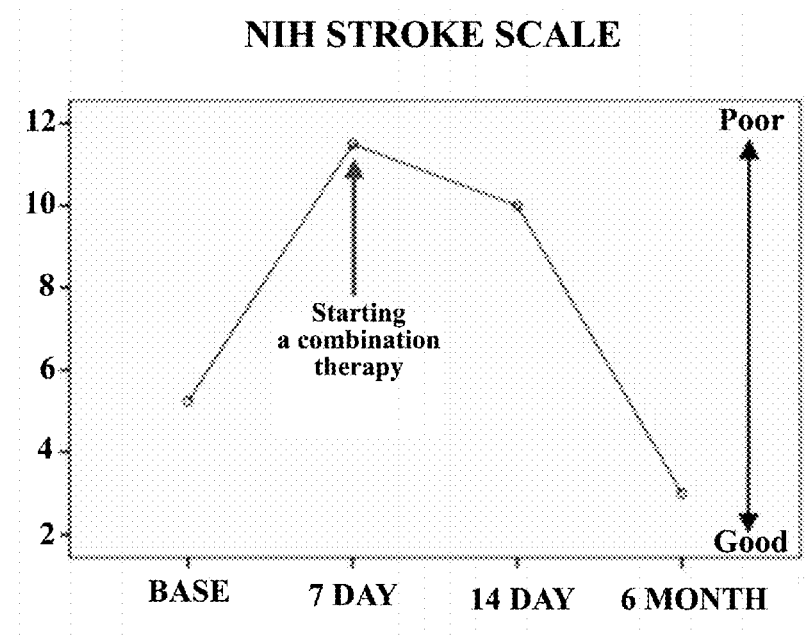

[Fig. 4]
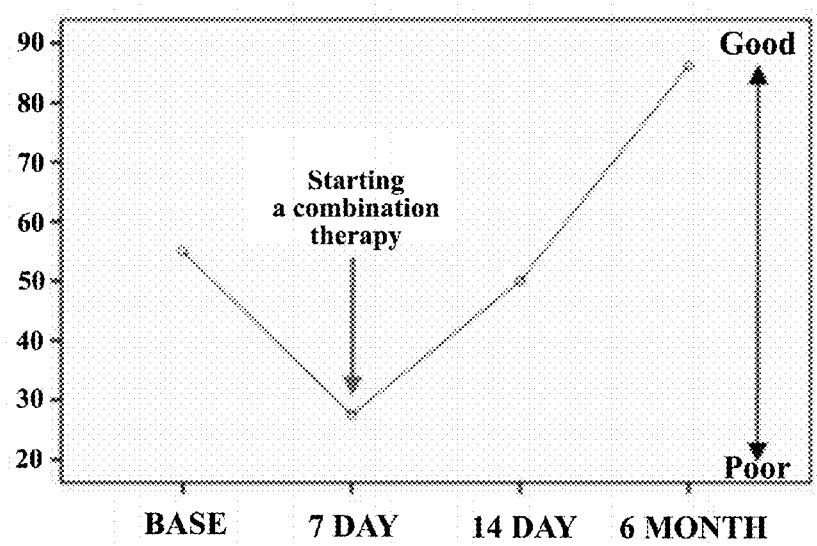

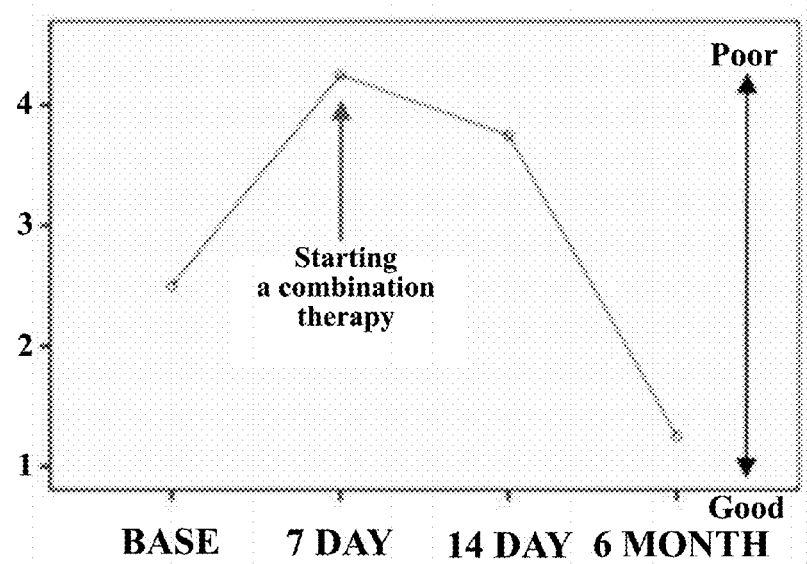
[Fig. 5]

[Fig. 6]
NIH STROKE SCALE
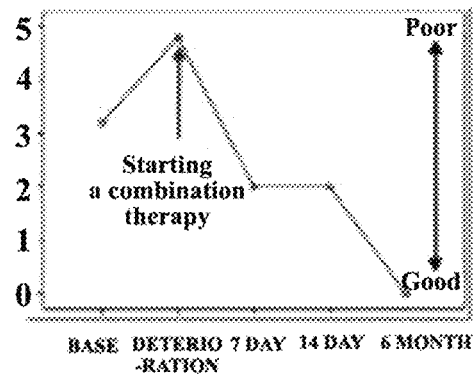
MODIFIED BARTHEL INDEX
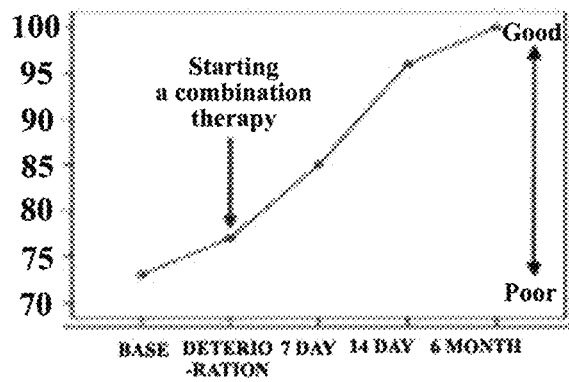
MODIFIED RANKIN SCALE
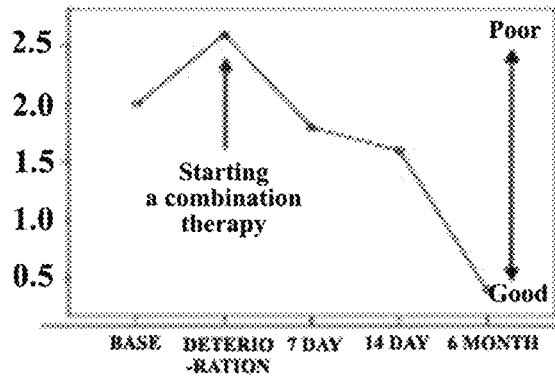

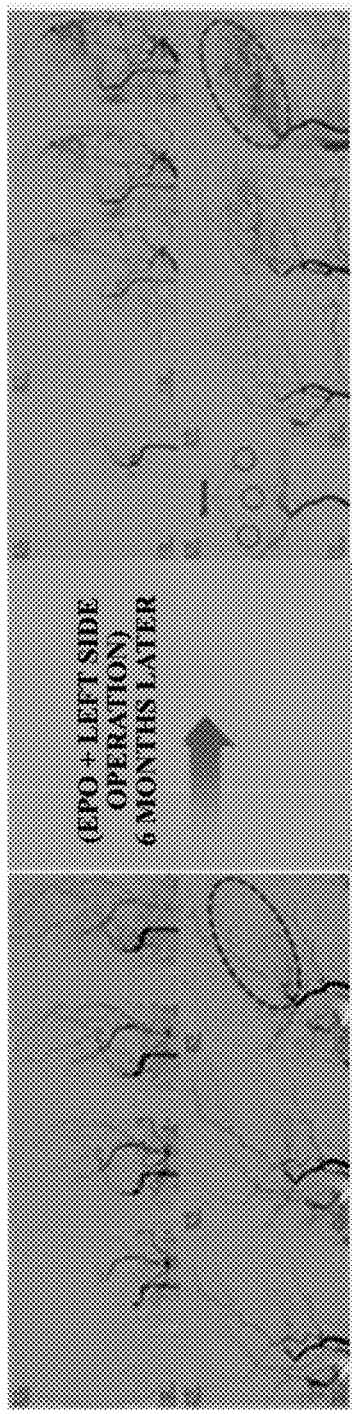
[Fig. 7]

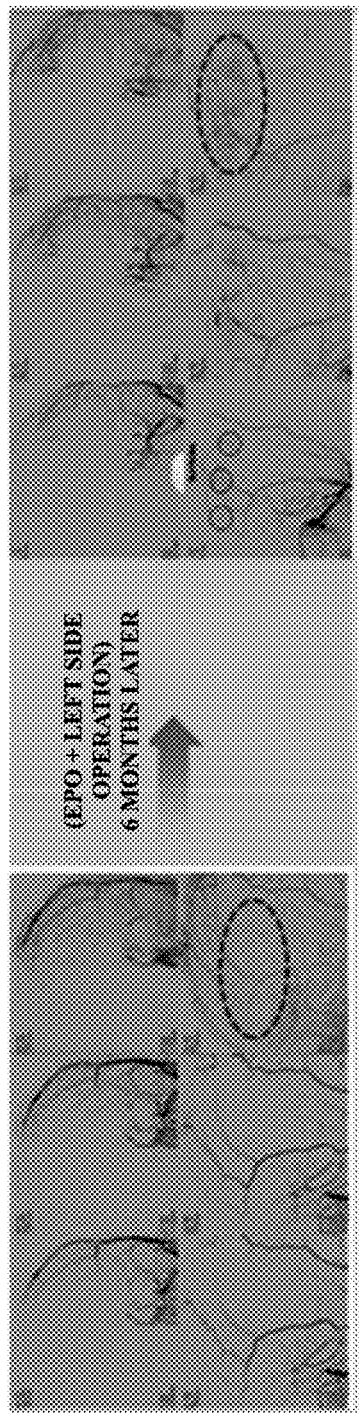
[Fig. 8]

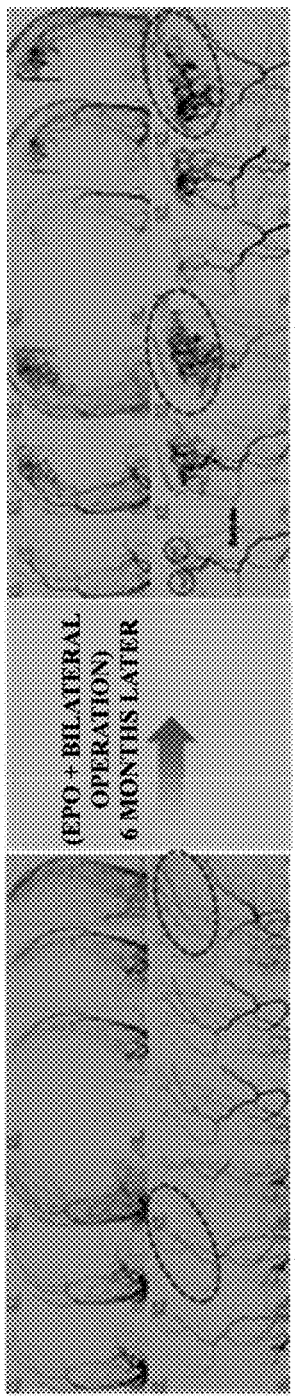
[Fig. 9]

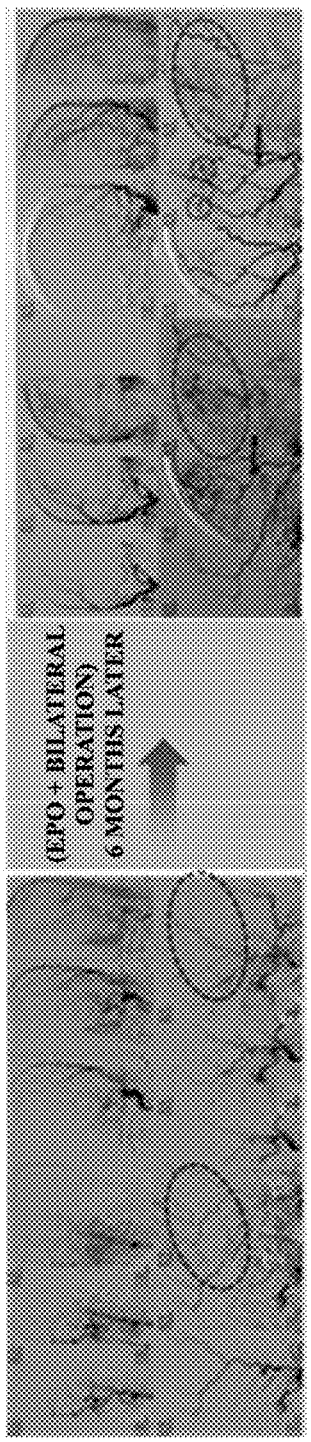
[Fig. 10]

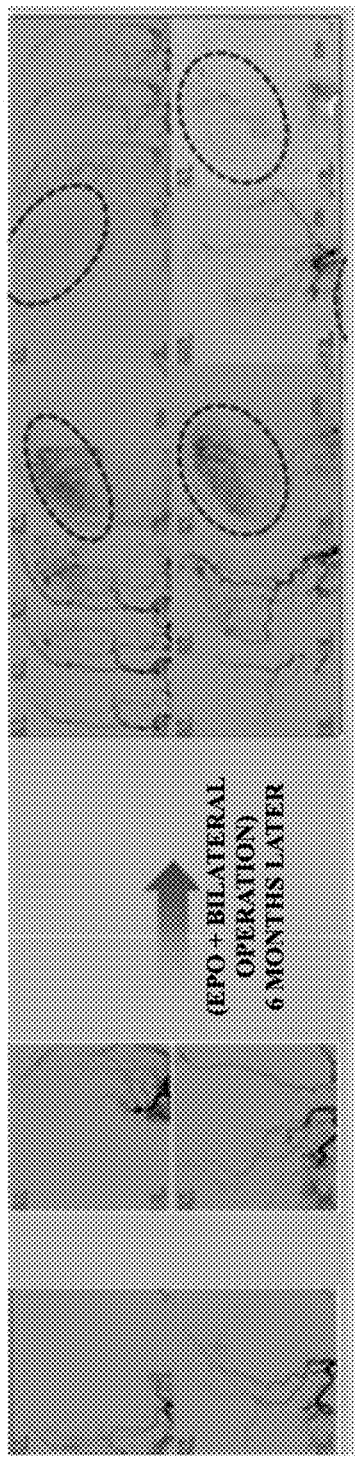

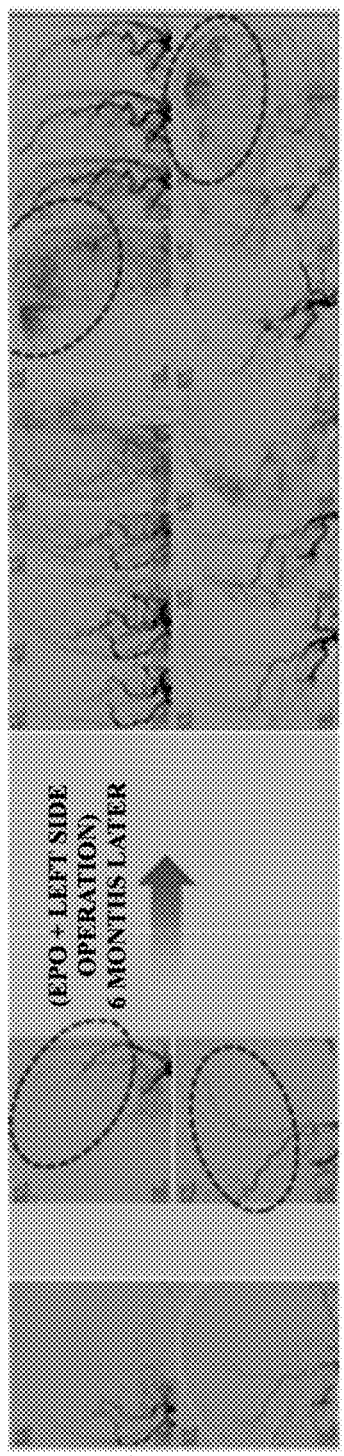
[Fig. 12]

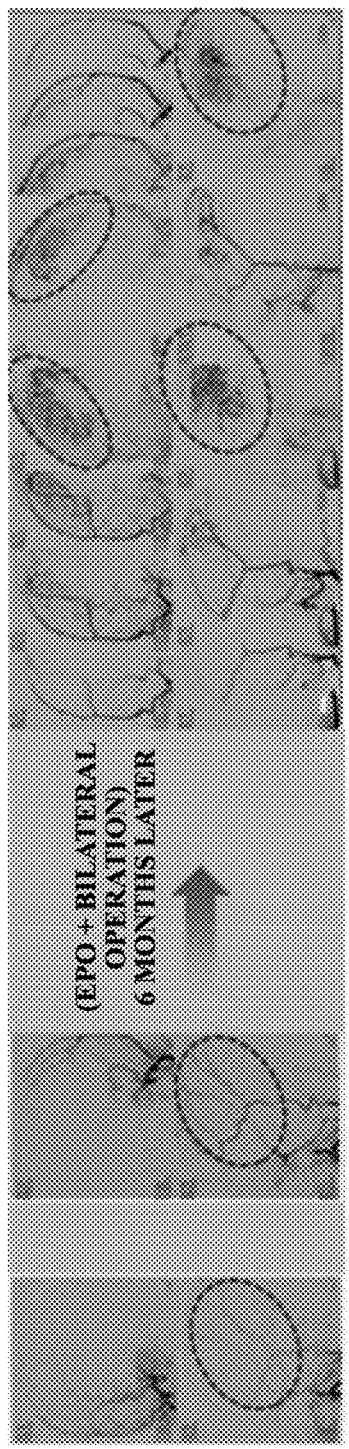
[Fig. 13]

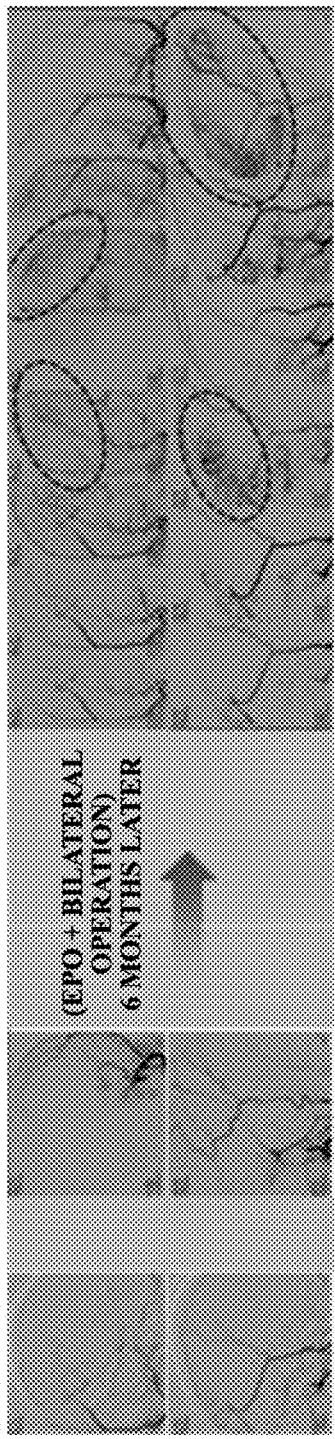
[Fig. 14]

[Fig. 15]
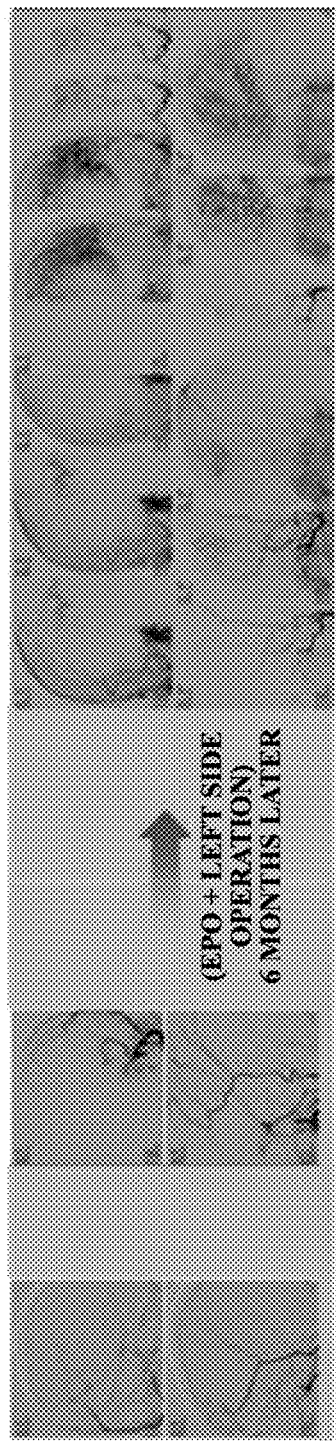

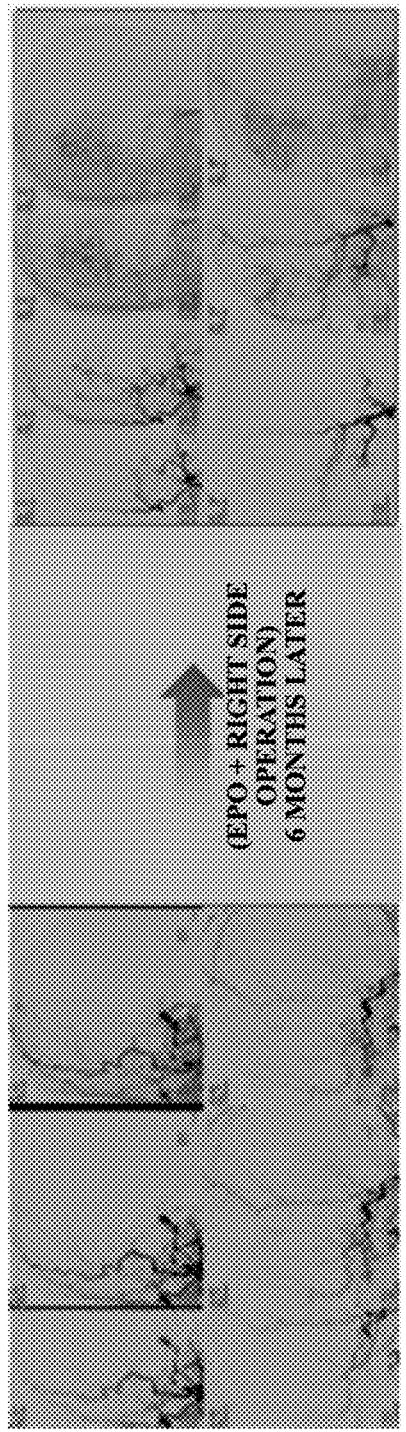

[Fig. 17]
BURRHOLE OPERATION
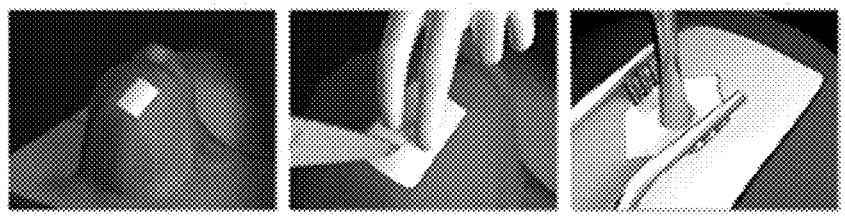
ONE WEEK STATES OF A PATIENT AFTER OPERATION
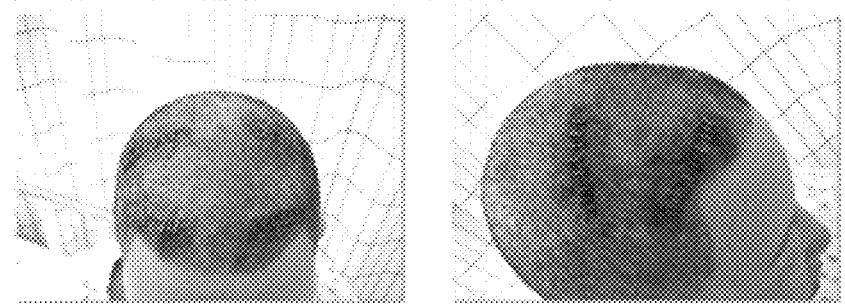

[Fig. 18]
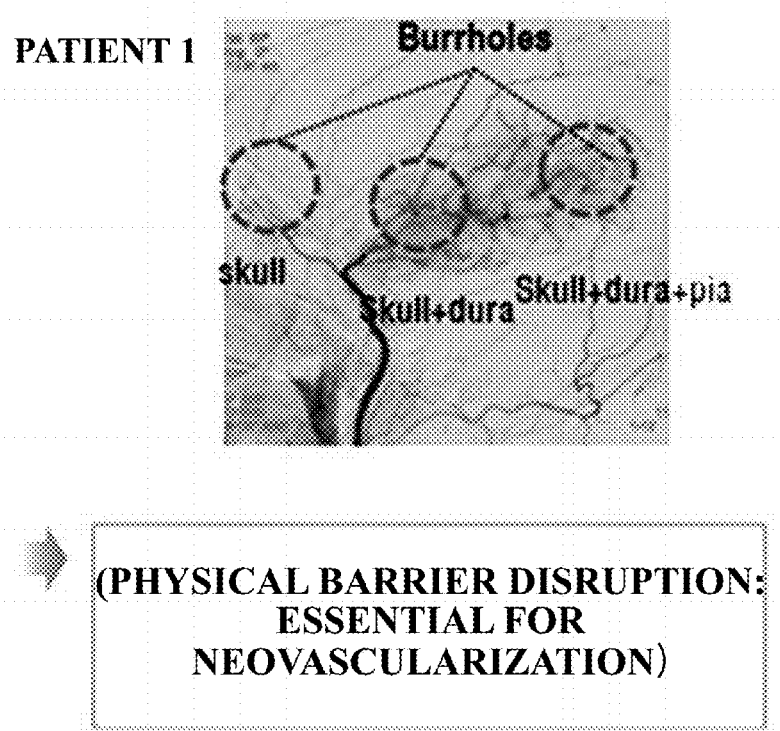

[Fig. 19]
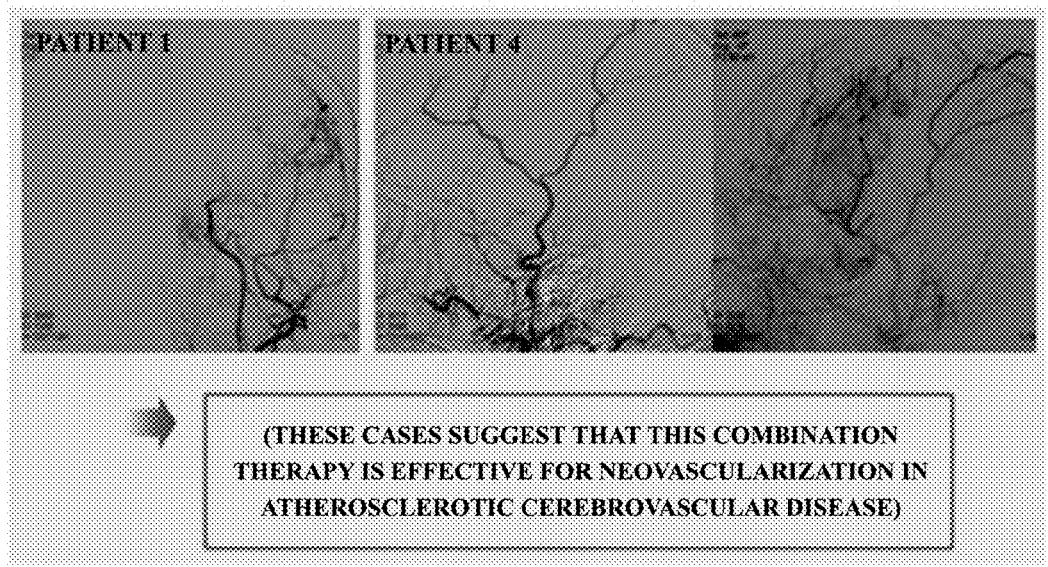

[Fig. 20]
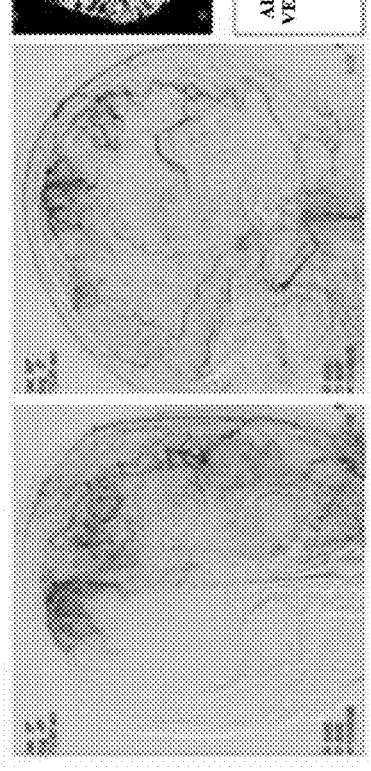
PATIENT 6 F/75
ADDITIONAL CASES WITH SUCCESSFUL FORMATION OF BLOOD VESSEL DETOUR FROM EXTRACRANIUM TO INTRACRANIUM IN ATHEROSCLEROTIC CEREBROVASCULAR OCCLUSION (CASE 6 AND CASE 8)
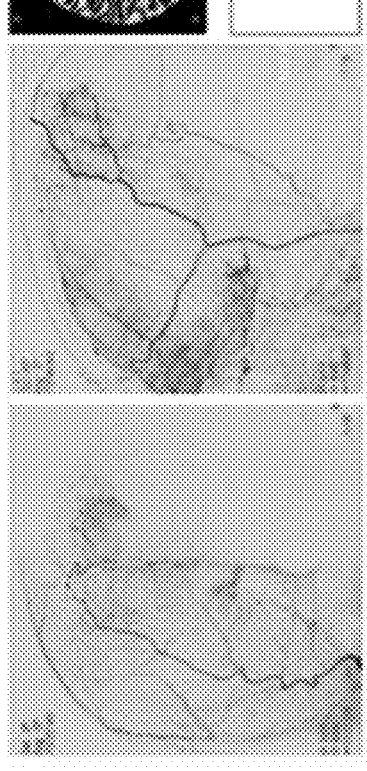
PATIENT 8 F/72
SUCCESSFUL NEOVASCULARIZATION EVEN IN VERY ELDERLY PATIENTS WITH MILD CEREBRAL PERFUSION DEFECT(CASES 6 AND 8)

[Fig. 21]
PATIENT 10 F/64
BEFORE TREATMENT 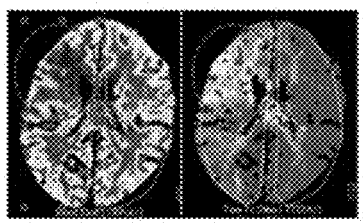 AFTER TREATMENT 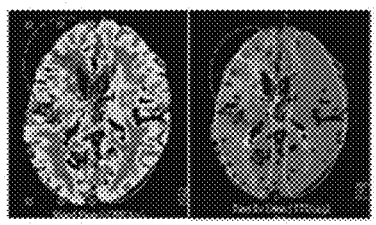

[Fig. 22]
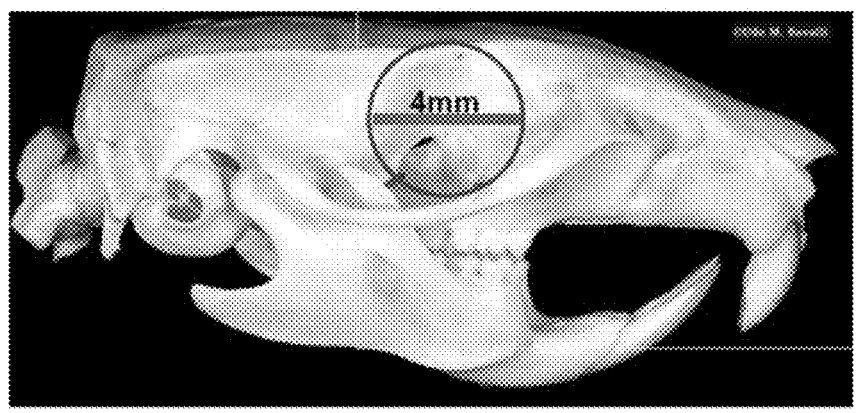

[Fig. 23]

[Fig. 24]
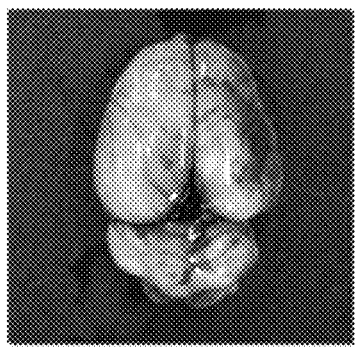 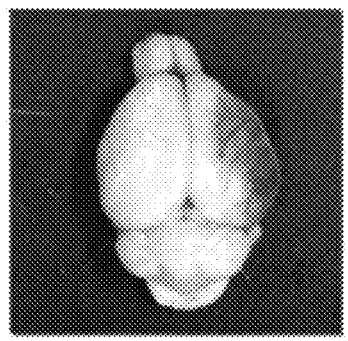

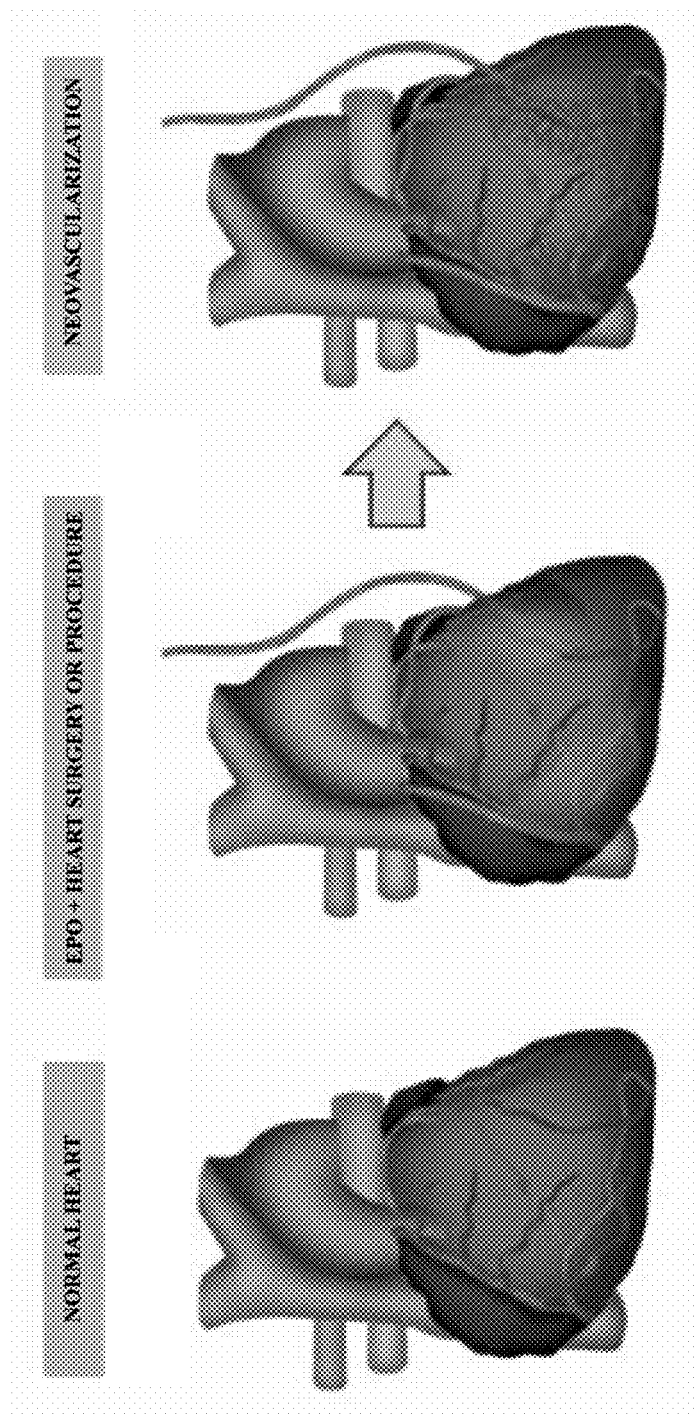

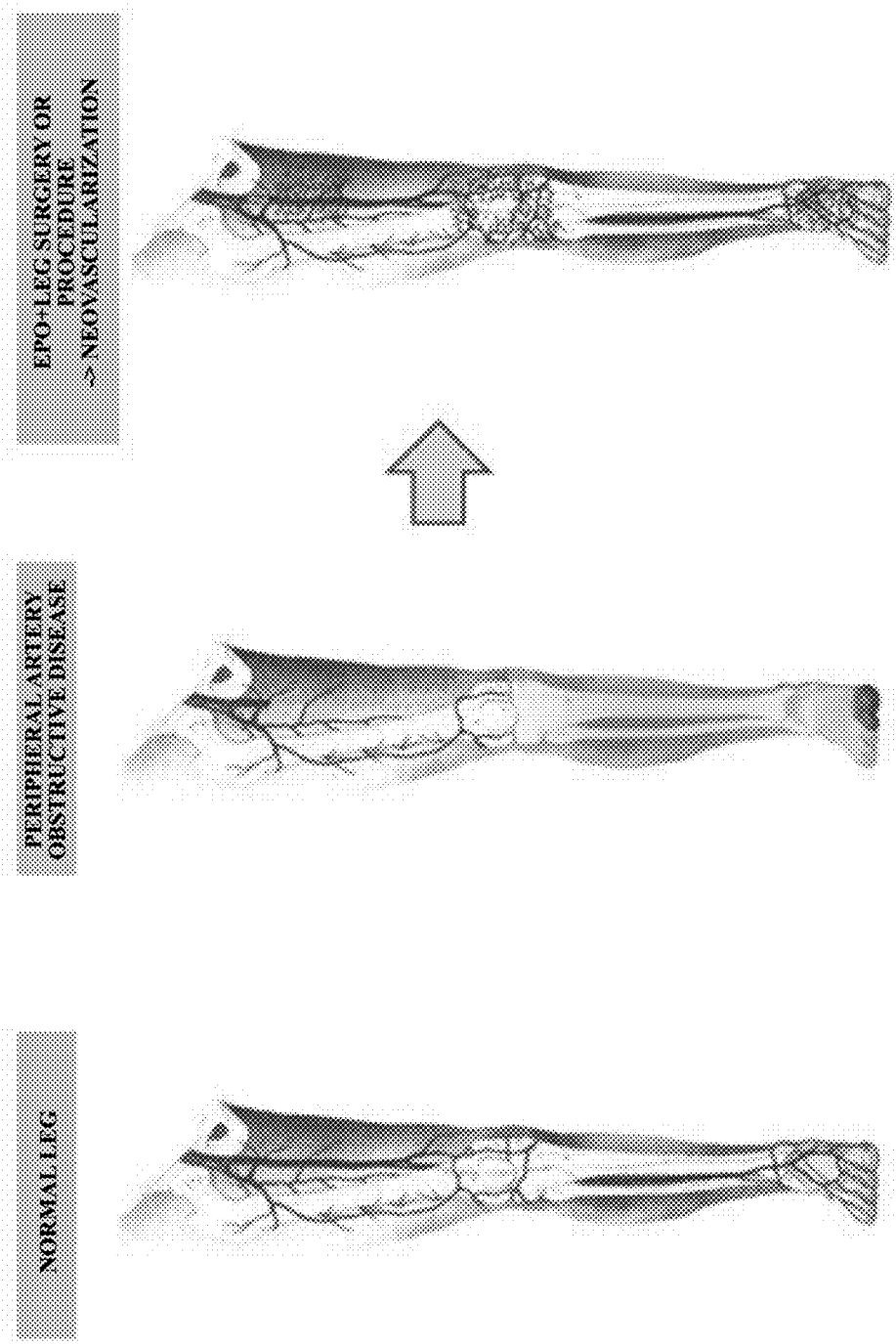
[Fig. 26]

COMPOSITION FOR AIDING SURGICAL PROCEDURES FOR TREATING ISCHEMIC VASCULAR DISEASES

CROSS-REFERENCE TO RELATED APPLICATIONS

This application is the U.S. national phase application filed under 35 U.S.C. § 371claiming benefit to International Patent Application No. PCT/KR2012/003260, filed on Apr. 26, 2012, which is entitled to priority under 35 U.S.C. § 119(a)-(d) to Korea application no. 10-2011-0039219, filed Apr. 26, 2011 and Korea application no. 10-2012-0043799, filed Apr. 26, 2012, each of which application is hereby incorporated herein by reference in its entirety.

TECHNICAL FIELD

The present invention relates to a composition for aiding surgical procedures for treating ischemic vascular diseases, and more specifically, to a composition, which contains erythropoietin (EPO) as an active ingredient, for aiding treatment of ischemic cerebrovascular diseases, ischemic cardiovascular diseases, or ischemic peripheral vascular diseases.

BACKGROUND ART

Ischemia is a restriction in blood supply to body organs, tissues, or body parts, causing eventually irreversible damage with necrosis of cells and tissues. In particular, the brain and the heart are body organs that are most susceptible to shortage of blood flow. When ischemia occurs in tissues caused by, for example, stroke or head injury, processes called ischemic cascade are caused and brain tissues are permanently damaged.

A cerebral infarction is caused by blockage or rupture of a blood vessel that supplies blood to the brain, which results in local damage of a brain, and is commonly called a "stroke." Stroke symptoms include, for example, hemiplegia, sensory disorders, language disorders, dysphonia, visual acuity and visual field disorders, diplopia, headache, dizziness, loss of consciousness, a vegetative state, and dementia. Strokes can be classified into two categories: ischemic and hemorrhagic. Ischemic strokes (80 to 85%) are those that are caused by completely blocked blood vessels or severely narrowed blood vessels of the brain, which can lead to insufficient blood flow to tissues. Hemorrhagic strokes (15 to 20%) are those that are caused by hemorrhaging, which can lead to functional loss of brain cells. Stroke is the second most frequent cause of death in Korea, and the third most frequent cause of death worldwide. Since about 50% or more of stroke survivors may have some type of disability, patients and caregivers have social burdens.

In ischemic strokes, which account for most strokes, a patient's prognosis may be mostly determined depending on clinical progress of an acute phase (within 7 days) or a subacute phase (within 4 weeks). Recanalization treatment is performed to resupply blood flow such that brain tissues of ischemic penumbrae, which are physiological marks of acute phase treatment in ischemic strokes, function again. However, it is currently known that recanalization therapy needs to be performed within 4.5 hours after the onset of symptoms with an intravenous injection or within 6 hours after the onset of symptoms with an intraarterial injection in order to improve the patient's prognosis. However, stroke patients around the world are rarely identified on time and treated with appropriate recanalization in an emergency room. Therefore, since most patients with acute ischemic strokes are not appropriately managed, safe, effective, and new therapy for acute phase patients is necessary.

Meanwhile, although ischemic cardiovascular diseases or ischemic peripheral vascular diseases, which are ischemic diseases within tissues, have a relatively longer time window than those of the brain, there are still many patients who miss timely treatments and do not receive appropriate care. Even when reperfusion is successfully performed within a time window after ischemic diseases occur in cardiac, brain, and peripheral tissues, paradoxically, in some cases, tissue damages further occur. This is called a reperfusion injury. It is known that such reperfusion injury easily occurs when a blood vessel is suddenly blocked rather than blocked slowly, when tissues have large ischemic lesions, and when a time of blood vessel blockage is longer. Therefore, when such injuries occur, since tissue damage further occurs, a reperfusion operation or therapy may often lead to a poor prognosis.

Ischemic diseases such as cerebral infarctions, myocardial infarctions, and peripheral arterial obstructive diseases are generally caused by shortage of blood supply, which eventually results in irreversible damage to cells constituting organs.

Up to now, in order to treat excitotoxicity, inflammation, and oxidative stress occurring in an early stage of the ischemic cascade, that is, a destructive phase of tissues, neuroprotective drugs have been developed, on which preclinical studies and clinical studies have been conducted. However, no significant effects on the human body have been found yet.

In addition to an acute phase stroke, in chronic obstructive ischemic cerebrovascular diseases (including moyamoya disease), therapy for improving intracranial blood flow has been developed using anastomosis in which a normal lateral intracranial blood vessel and an abnormal intracranial blood vessel are attempted to be connected. Such vascular anastomosis is divided into two categories depending on treatment methods: direct and indirect. In direct vascular anastomosis, intra- or extra-cranial blood vessels are directly connected. In indirect vascular anastomosis, intra- or extra-cranial blood vessels are not directly connected. In direct vascular anastomosis, an extra-cranial blood vessel is dissected, and then a cranium is disruptiond, and an abnormal intracranial blood vessel is found and connected. In indirect vascular anastomosis, procedures are the same as above, but intra- or extra-cranial blood vessels are not directly connected. Therefore, a long operation time under general anesthesia, and skilled professionals are necessary. Particularly, the direct vascular anastomosis is highly dependent on surgeons, and thus even trustworthy medical institutions have reported postoperative cerebral infarctions in about 21% of cases and a mortality rate of about 9%. The indirect vascular anastomosis is a relatively simpler operation than the direct vascular anastomosis. However, due to premises of postoperative neovascularization, it may be applied only to pediatric patients who have better cerebral neovascularization environments and conditions than adults. In addition, although the indirect vascular anastomosis is a relatively simpler operation than the direct vascular anastomosis, operation side effects still occur and about 15% of postoperative patients have side effects such as cerebral infarctions. Accordingly, the anastomosis has been difficult to attempt in acute phase stroke treatment. Alternatively, a multiple burrhole operation is safe therapy having few complications, has a short operation time under local anesthesia, is non-dependent on surgeons, and a clinician may monitor and manage changes in a patient's condition during the procedure.

Meanwhile, it has been reported that neovascularization is induced from a meningeal artery and a moyamoya blood vessel disappears when the multiple burr-hole operation is performed on a plurality of adult moyamoya patients (J Korean Neurosurg Soc 35:17-22, 2004, Ko Youngsam et al.). However, since this operation was not performed in acute phase stroke patients, and neovascularization was not induced in all patients, this operation is not being actively applied worldwide. Korea Patent No. 10-0774827 discloses that when erythropoietin is locally administered in ischemic brain tissues, significant neuroprotective effects occur, and thus an area of permanently damaged brain tissues is decreased. However, this patent literature mentions only the neuroprotective effects. In addition, US Patent Publication No. 2010-0247452 discloses that erythropoietin improves differentiation and adhesion of endothelial progenitor cells, and thus neovascularization may be induced from tissues or organs in which a blood vessel is formed or from which a blood vessel formation stimulus is released. However, this patent literature does not mention or provide a concept of a physical barrier of a living body.

DISCLOSURE

Technical Problem

In surgical procedures for treating ischemic vascular diseases such as ischemic cerebrovascular diseases, ischemic cardiovascular diseases, and ischemic peripheral vascular diseases, when erythropoietin is used as a neovascularization inducer for aiding treatment (or operation) in which a physical barrier is minimally invaded, it is understood that neovascularization is induced by the treatment, ischemic-reperfusion injury decreases, and thus ischemic diseases may be effectively treated. As a result, the inventor has completed this invention.

The invention provides a composition, which contains erythropoietin (EPO) as an active ingredient, for aiding surgical procedures for treating ischemic vascular diseases. In addition, the invention provides a method for surgical procedures of ischemic cerebrovascular diseases, ischemic cardiovascular diseases, and ischemic peripheral vascular diseases using the composition containing EPO as an active ingredient.

However, the technological scope of the present invention is not limited to the aforementioned scope but other scopes, which are not mentioned above, may be clearly understood by those skilled in the art by the following description.

Technical Solution

In view of the aforementioned problems, one aspect of the present invention provides a composition, which contains erythropoietin (EPO) as an active ingredient, for aiding surgical procedures for treating ischemic vascular diseases. The ischemic vascular diseases may include, for example, ischemic cerebrovascular diseases, ischemic heart diseases, and ischemic peripheral vascular diseases.

The surgical procedures of the ischemic vascular diseases may include, for example, vascular intervention, a burrhole operation, direct vascular anastomosis, and indirect vascular anastomosis.

The composition may be administered before surgical procedures of ischemic vascular diseases.

The composition may reduce ischemic-reperfusion injury after surgical procedures of ischemic cardiovascular diseases or ischemic peripheral vascular diseases.

The composition may be administered to induce neovascularization after surgical procedures for connecting intra- or extra-cranial blood vessels in ischemic cerebrovascular diseases.

The composition may be administered to a patient with an acute phase vascular occlusion.

Another aspect of the present invention provides a method for treatment of ischemic vascular diseases including administration of the composition to a patient who needs surgical procedures of ischemic vascular diseases. The composition may be administered before or after surgical procedures of ischemic vascular diseases, and preferably, may be administered to a patient before surgical procedures of ischemic vascular diseases. The ischemic vascular diseases according to the invention may include, for example, ischemic cerebrovascular diseases, ischemic cardiovascular diseases, and ischemic peripheral vascular diseases.

In the method, the composition may be administered to a patient with an acute phase vascular occlusion.

Advantageous Effects

When various surgical procedures including the multiple burr-hole operation are performed on adult patients occurred ischemic cerebrovascular diseases, ischemic cardiovascular diseases or ischemic peripheral vascular diseases including moyamoya disease using the EPO-containing composition according to the invention, it is possible to maximize a neovascularization mechanism quickly, and to perform safe, simple, and effective treatment using a neovascularization mechanism. As a result, it is possible to significantly increase a success rate of procedures.

DESCRIPTION OF DRAWINGS

FIG. 1 is a diagram illustrating a strategy for stroke treatment using blood vessel formation according to the invention.

FIG. 2 is a schematic diagram illustrating neovascularization and brain function recovery according to an embodiment of the invention.

FIG. 3 is a graph illustrating a change of an average value of NIH stroke scales of patients 1 to 4 over time.

FIG. 4 is a graph illustrating a change of an average value of modified barthel indexes of patients 1 to 4 over time.

FIG. 5 is a graph illustrating a change of an average value of modified Rankin scales of patients 1 to 4 over time.

FIG. 6 is a graph illustrating changes of an average value of NIH stroke scales, an average value of modified barthel indexes, and an average value of modified Rankin scales of patients 5 to 10 over time.

FIG. 7 includes pictures showing cerebrovascular images captured before and after treatment when a composition for aiding blood vessel formation was administered and a multiple burr-hole operation was performed in order to treat an acute ischemic brain disease in patient 1 according to an embodiment of the invention.

FIG. 8 includes pictures showing cerebrovascular images captured before and after treatment when a composition for aiding blood vessel formation was administered and a multiple burr-hole operation was performed in order to treat an acute ischemic brain disease in patient 2 according to an embodiment of the invention.

FIG. 9 includes pictures showing cerebrovascular images captured before and after treatment when a composition for aiding blood vessel formation was administered and a multiple burr-hole operation was performed in order to treat an acute ischemic brain disease in patient 3 according to an embodiment of the invention.

FIG. 10 includes pictures showing cerebrovascular images captured before and after treatment when a composition for aiding blood vessel formation was administered and a multiple burr-hole operation was performed in order to treat an acute ischemic brain disease in patient 4 according to an embodiment of the invention.

FIG. 11 includes pictures showing cerebrovascular images captured before and after treatment when a composition for aiding blood vessel formation was administered and a multiple burr-hole operation was performed in order to treat an acute ischemic brain disease in patient 5 according to an embodiment of the invention.

FIG. 12 includes pictures showing cerebrovascular images captured before and after treatment when a composition for aiding blood vessel formation was administered and a multiple burr-hole operation was performed in order to treat an acute ischemic brain disease in patient 6 according to an embodiment of the invention.

FIG. 13 includes pictures showing cerebrovascular images captured before and after treatment when a composition for aiding blood vessel formation was administered and a multiple burr-hole operation was performed in order to treat an acute ischemic brain disease in patient 7 according to an embodiment of the invention.

FIG. 14 includes pictures showing cerebrovascular images captured before and after treatment when a composition for aiding blood vessel formation was administered and a multiple burr-hole operation was performed in order to treat an acute ischemic brain disease in patient 8 according to an embodiment of the invention.

FIG. 15 includes pictures showing cerebrovascular images captured before and after treatment when a composition for aiding blood vessel formation was administered and a multiple burr-hole operation was performed in order to treat an acute ischemic brain disease in patient 9 according to an embodiment of the invention.

FIG. 16 includes pictures showing cerebrovascular images captured before and after treatment when a composition for aiding blood vessel formation was administered and a multiple burr-hole operation was performed in order to treat an acute ischemic brain disease in patient 10 according to an embodiment of the invention.

FIG. 17 is a schematic diagram illustrating a burrhole operation performed on patients 1 to 10 , and a figure and a diagram showing states one week later of patients after a bilateral operation according to an embodiment of the invention.

FIG. 18 is a picture showing whether cerebrovascular neovascularization occurred according to a method of removing various anatomical barriers of a cranium when a composition for aiding blood vessel formation and a multiple burr-hole operation was performed in order to treat an acute ischemic brain disease in patient 1 according to an embodiment of the invention.

FIG. 19 is a cerebrovascular picture showing that neovascularization was successful for atherosclerotic cerebrovascular occlusion when a composition for aiding blood vessel formation is administered and a multiple burr-hole operation was performed in order to treat acute ischemic brain diseases in patients 1 and 4 according to an embodiment of the invention.

FIG. 20 is a cerebrovascular picture showing that neovascularization was successful for atherosclerotic cerebrovascular occlusion in elderly patients when a composition for aiding blood vessel formation was administered and a multiple burr-hole operation was performed in order to treat acute ischemic brain diseases in patients 6 and 8 according to an embodiment of the invention.

FIG. 21 are pictures showing perfusion images indicating a significant increase in cerebral blood flow before and after treatment when a composition for aiding blood vessel formation was administered and a multiple burr-hole operation was performed in order to treat an acute ischemic brain disease in patient 10 according to an embodiment of the invention.

FIG. 22 is a schematic diagram illustrating a model when a minimally invasive operation was performed on rats.

FIG. 23 is a picture showing a degree of neovascularization in three groups (group 1 with only drug administration, group 2 with only a burrhole operation, and group 3 with drug administration and a burrhole operation) when drug administration and an operation were performed on rats in order to observe neovascularization caused by EPO and a burrhole operation in a model designed for rats.

FIG. 24 is a picture showing a degree of neovascularization when combination therapy of EPO, a burrhole operation, and rh-VEGF-A165 is performed in a model designed for rats.

FIG. 25 is a schematic diagram illustrating neovascularization and cardiac function recovery according to an embodiment of the invention.

FIG. 26 is a schematic diagram illustrating neovascularization and recovery of a peripheral tissue function according to an embodiment of the invention.

MODES OF THE INVENTION

In surgical procedures for treating ischemic vascular diseases such as ischemic cerebrovascular diseases, ischemic cardiovascular diseases, and ischemic peripheral vascular diseases, when erythropoietin (EPO) is used as a neovascularization inducer for aiding treatment (or operation) in which a patient's physical barrier is minimally invaded in order to reduce a patient's complications as much as possible, a neovascularization mechanism in ischemic blood vessel diseases such as ischemic cerebrovascular diseases, ischemic cardiovascular diseases, and ischemic peripheral vascular diseases is quickly maximized so that treatment of acute stage blood vessel diseases in which continuous tissue damages occur is safely, simply, and effectively performed using neovascularization mechanism. In ischemic diseases, EPO is administered before treatment so that neovascularization is induced by the treatment, ischemic-reperfusion injury decreases, and thus ischemic diseases may be effectively managed. As a result, the inventor has completed this invention.

The invention provides a composition, which contains EPO as an active ingredient, for aiding surgical procedures for treating ischemic vascular diseases, and a method for treatment of ischemic vascular diseases using the composition.

Specifically, currently, neuroprotective effects of EPO have been reported in animals, but there is no concept or inferred result that a certain substance or method disruptions an intra- or extra-cranial anatomical barrier in a human body and laboratory animals with acute phase cerebral ischemia using a simple operation, neovascularization regeneration is induced through a concept of normal extracranial diffusion from, and the regenerated neovascularization is used intracranially in acute ischemic tissues. Therefore, the invention provides a method in which EPO, which is very safe to living bodies, and a growth factor protein are used to safely and effectively improve neovascularization regeneration in ischemic tissues of acute cerebral infarctions of patients and animals. In addition, validity of the method is proved so that a new function of the composition is verified in a living body.

In this specification, the term "erythropoietin (EPO)" refers to a glycoprotein produced by interstitial tissues in a kidney of an adult or in a liver of a fetus. Since EPO and a receptor thereof increase hemoglobin by protecting against apoptosis of erythroid progenitor cells in bone marrow, it has been generally used for anemia treatment of chronic renal failure patients. Hypoxia and ischemia in tissues are important factors that directly cause expression of EPO in the brain. In an ischemic reperfusion experimental model, neuroprotection has been observed and anti-apoptosis effects have been reported. In addition, EPO helps a vascular endothelial growth factor (VEGF) when endothelial cells are produced, and is directly or indirectly involved in, for example, microvascular formation and artery formation.

In this specification, the term "ischemic vascular disease" refers to a disease directly or indirectly involving blood vessels, and includes a disease in which a blood flow amount is reduced due to blood vessel disorders or a disease that develops from the reduced blood flow. The ischemic vascular disease includes, for example, ischemic cerebrovascular diseases, ischemic heart diseases, and ischemic peripheral vascular diseases, and the invention is not limited thereto.

In this specification, the term "ischemic cerebrovascular disease" refers to a disease that occurs when blood is not properly supplied to blood vessels of the brain. The ischemic cerebrovascular disease includes, for example, ischemic stroke, moyamoya disease, cerebral thrombosis, and cerebral embolism, and the invention is not limited thereto.

In this specification, the term "ischemic stroke" is also called "cerebral infarction" and refers to an irreversible condition of brain tissue necrosis caused by reduced blood supply to the brain.

In this specification, the term "moyamoya disease" refers to a disease in which stenosis or occlusion appears at the end of an internal carotid artery, or at the beginning of an anterior cerebral artery and a middle cerebral artery in the cranial cavity for no specific reason, and generation of an abnormal blood vessel called a "moyamoya blood vessel" is observed in the vicinity thereof.

In this specification, the term "cerebral thrombosis" refers to a disease that occurs when a passage disorder of blood flow is generated due to artery luminal stenosis or thrombosis caused by arteriosclerosis of a certain cerebrovascular part.

In this specification, the term "cerebral embolism" refers to a disease that occurs when a cerebral vessel is blocked caused by thrombosis generated from the heart.

In this specification, the term "ischemic cardiovascular disease" refers to a disease that occurs when blood is not properly supplied to cardiac-related blood vessels. The cardiovascular disease includes, for example, myocardial infarction and angina pectoris, and the invention is not limited thereto.

In this specification, the term "myocardial infarction" refers to a disease in which acute occlusion of coronary arteries of the heart occurs due to, for example, thrombosis or spasm, and thus tissues or cells in the heart muscle become necrotic.

In this specification, the term "angina pectoris" refers to a disease in which blood supply to whole or a part of heart is decreased, oxygen and nutrition supply is drastically reduced, and thus heart muscles maintain a secondary ischemic condition.

In this specification, the term "ischemic peripheral vascular disease" refers to a blood vessel disease that occurs when blood flow is not properly supplied to arteries and veins of a limb. The peripheral vascular disease includes, for example, peripheral vascular stenosis and peripheral vascular occlusion, and the invention is not limited thereto.

In this specification, the term "peripheral vascular stenosis" refers to a disease in which arteries or veins of the limb are narrowed due to, for example, aging.

In this specification, the term "peripheral vascular occlusion" refers to a disease in which arteries or veins of the limb are blocked due to, for example, aging.

In this specification, the term "aneurysm" refers to a disease in which an arterial wall bulges locally in the shape of a hump.

In this specification, the term "surgical procedures of ischemic vascular diseases" refers to surgical procedures for treatment of ischemic vascular related diseases. The treatment for ischemic vascular related diseases includes, for example, vascular intervention, direct vascular anastomosis, and indirect vascular anastomosis, and the invention is not limited thereto.

In this specification, the term "vascular intervention" refers to a therapeutic procedure of moving into a blood vessel rather than an operation for treatment of a disease occurring in the blood vessel. The vascular intervention includes, for example, balloon angioplasty and stent graft, and the invention is not limited thereto.

In this specification, the term "balloon angioplasty" refers to a procedure of inserting a thin and soft thread-like wire and a balloon catheter having a small balloon at the tip of the catheter through an inguinal or arm blood vessel, the balloon catheter is guided to a region in which a blood vessel is blocked, and then is inflated to expand the blood vessel.

In this specification, the term "stent graft" refers to a procedure of using a balloon catheter having a stent, a fine mesh-like device made of metal, when balloon angioplasty is performed, the stent is expanded according to inflation of the balloon catheter, and the expanded stent is used to maintain an expanded blood vessel.

In this specification, the term "indirect vascular anastomosis" refers to a procedure of inducing formation of a blood vessel which supplies blood to the brain such that scalp arteries, meninges, or muscles simply come into contact with the outer surface. The indirect vascular anastomosis includes a multiple burr-hole operation, and the invention is not limited thereto.

In this specification, the term "ischemic-reperfusion injury" refers to tissue damage that occurs due to blood flow recovery to ischemic tissues in which an acute ischemic condition occurs and oxidation, and particularly, includes a microvascular disorder. Disorders occur when endothelial cell functions in all segmentations (arterioles, capillaries, and venules) of the microvasculature are exposed to ischemic-reperfusion. This endothelial cell disorder is manifested as an impaired ability of arterioles to vasodilate, enhanced fluid filtration and leukocyte plugging in capillaries, and increased leukocyte-endothelial cell adhesion and protein extravasation in venules. An imbalance in the production of reactive oxygen species and nitric oxide (NO) promote these responses.

In this specification, the term "multiple burr-hole operation" refers to a surgery in which a drill that stops automatically on the dura mater is used to perforate multiple holes in the cranium. Since the surgery is a simple procedure, there are no technical issues such as a surgeon's surgical skill and it can be simply performed under local anesthesia.

The composition for aiding surgical procedures for treating ischemic vascular diseases according to the invention may be used alone for treatment of ischemic vascular diseases, or may be administered along with surgery, hormone therapy, medication, and methods using a biological response modifier.

In conventional treatment of ischemic vascular diseases, various surgical procedures such as vascular intervention or indirect vascular anastomosis have been used. However, the procedures may not be performed on patients in an acute phase or at high-risk. Therefore, research on developing a method of inducing blood vessel formation using, for example, EPO, has been actively underway. However, only a result that EPO helps VEGF and is involved in blood vessel formation has been obtained, and a clinical case in which EPO is clinically applied to treat ischemic diseases and neovascularization substantially succeeds has not been reported.

Anatomically, when EPO or a certain blood vessel formation inducing substance is used alone, a method of inducing blood vessel formation does not show sufficient effects due to a physical barrier. Anatomically, branches of internal carotid arteries and external carotid arteries, which are intra- or extra-cranial blood vessels, may not be connected each other due to physical barriers such as a cranial bone and meninges. Therefore, when an intracranial blood vessel disorder occurs, branches of external carotid arteries that supply blood to the scalp may not supply blood to the cranial cavity without perforation of such physical barriers. Without perforation of physical barriers, it is difficult to use normal blood flow of external carotid arteries in the cranial cavity. In addition, physiologically, when EPO or a certain blood vessel formation inducing substance is used alone, only microvasculature, which is less effective in terms of a blood flow amount, is produced (angiogenesis), and it is difficult to produce a blood vessel (vasculogenesis), that can supply sufficient blood flow necessary for actual treatment of ischemic diseases. The concept of such physical barrier is also applied to peripheral vascular obstructive diseases. That is, when a clogged blood vessel is a proximal area, a length of a blood vessel to be generated by EPO or a blood vessel formation inducer is excessive. Therefore, when EPO is administered alone, since a length of a blood vessel to be formed is excessive, it is difficult to produce a sufficient blood vessel necessary for treatment. As a result, when a procedure or surgery of destroying a physical barrier on the length is used along with a blood vessel formation inducer, it is possible to induce neovascularization of a desired region.

In addition, in ischemic cardiovascular diseases or ischemic peripheral vascular diseases such as cardiac ischemia and peripheral arterial obstructive diseases, which have a relatively long time window for reperfusion treatment, there were problems in that prognosis is poor due to side effects caused by postoperative ischemic-reperfusion injury for blood flow recovery to ischemic tissues.

Accordingly, the inventor has developed a new method in which EPO is safely preprocessed before the therapeutic procedure and various signals conditioning blood vessel formation or tissue ischemia are induced, thereby overcoming problems of the above methods.

That is, unlike conventional neuroprotection methods for treating excitotoxicity and inflammation occurring in an early stage (destructive phase) of ischemic diseases, the inventor has succeeded in inducing a stronger and quicker mechanism of blood vessel formation, which appears in a late stage (regenerative phase) of ischemic diseases. As a result, it is possible to achieve fundamental and effective treatment for acute phase ischemic diseases (refer to FIG. 1).

Actually, in treatment of moyamoya disease or an obstructive artery disease, which is one of ischemic cerebrovascular diseases, when EPO is administered to patients to cause a neovascularization signal first, and a multiple burr-hole operation for destroying only a cranium and meninges serving as intra- or extra-cranial barriers is performed in parallel, blood vessels are sufficiently produced in whole brain tissues. As a result, more significant treatment effects have been observed than when each method is performed independently.

In addition, in ischemic cardiovascular diseases or ischemic peripheral vascular diseases such as cardiac ischemia and peripheral arterial obstructive diseases, when EPO is preprocessed for conditioning a blood vessel formation inducing signal before and after an operation for blood flow recovery to ischemic tissues, side effects caused by postoperative ischemic-reperfusion injury are significantly reduced (refer to FIGS. 25 and 26).

According to an embodiment of the invention, the composition of the invention may include a pharmaceutically acceptable carrier in addition to EPO.

The carrier includes any standard pharmaceutical carrier used in known dosage forms such as sterile solutions, tablets, coated tablets, and capsules, and the invention is not limited thereto. Typically, the carrier includes diluting agents, for example, lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methyl hydroxybenzoate, propyl benzoate, talc, magnesium stearate, polyvinylpyrrolidone, dextrin, milk, a certain type of clay, stearic acid, talc, vegetable oils (for example, cooking oil, cottonseed oil, coconut oil, almond oil, and peanut oil), an oil-type ester such as triglyceridic acid, mineral oil, vaseline, animal fats, and cellulose derivatives (for example, crystallized cellulose, hydroxypropylcellulose, hydroyxpropylmethylcellulose, and methylcellulose), or other known diluting agents. Such a carrier may also include antioxidants, humectants, viscosity stabilizers, flavor agents, coloring additives, and other ingredients.

According to another embodiment of the invention, the composition of the invention includes EPO as an active ingredient, and may be formulated in various dosage forms including a pharmaceutically acceptable carrier.

The formulation includes oral administration, parenteral preparations, or external application such as soft capsules, hard capsules, tablets, and syrups, and the invention is not limited thereto. More specifically, solid formulations for oral administration include, for example, tablets, pills, powders, granules, and capsules. Formulations for parenteral administration include sterile aqueous solutions, non-aqueous solvents, suspensions, emulsions, lyophilized formations, and suppositories.

In addition, the present invention provides a method for surgical procedures for treating ischemic vascular diseases including administering an EPO-containing composition of the invention to patients before or after ischemic vascular disease treatment. Preferably, before acute phase ischemic vascular disease treatment, the EPO-containing composition of the invention may be administered to patients. The ischemic vascular diseases of the invention include, for example, ischemic cerebrovascular diseases, ischemic cardiovascular diseases, and ischemic peripheral vascular diseases.

Administration routes of the composition according to the invention may include any general route that can reach target tissues, for example, oral administration, intraperitoneal administration, intravenous injection, intramuscular injection, subcutaneous injection, intradermal injection, intranasal administration, intrapulmonary administration, intrarectal administration, intracavitary injection, intraperitoneal injection, and intradural administration, and the invention is not limited thereto. The composition according to the invention may be administered daily or intermittently before treatment, and may be administered once per day or administered in 2 or 3 divided doses. Preferably, 10 days before the treatment, the composition for aiding is administered for three days at a dose of 40,000 IU, and the treatment is performed under local anesthesia seven days later. However, the administration method and dosage of the composition are not limited thereto, and administration is appropriately performed by various methods known in those skilled in the art in consideration of, for example, a type of disease, a type of administration, and treatment effects.

Hereinafter, exemplary examples of the invention will be described to promote understanding of the invention. However, the following examples should be considered in a descriptive sense only and the scope of the invention is not limited to the following examples.

EXAMPLE 1

Neovascularization Using Combination Therapy of Acute Cerebral Infarction of Patients In patients with acute cerebral infarctions (within one week after onset of symptoms), in order to verify neovascularization and treatment effects of combination therapy [multiple burr-hole operation+EPO infusion], the combination therapy was performed on patients of acute cerebral infarctions caused by large artery atherosclerotic ischemic stroke or adult-type moyamoya patients. Then, clinical manifestations and a change of neovascularization before and after treatment were measured.

EXAMPLE 1-1

Multiple Burr-Hole Operation for Treatment of Moyamoya Patients

Among adult patients aged 18 years and older whose clinical features had been observed for six months or more and were identified as acute cerebral infarctions in diffusion weighted images, EPO was administered to 10 subjects (patients 1 to 10), which include acute cerebral infarctions caused by large artery atherosclerotic ischemic stroke (n=5) and adult-type moyamoya patients (n=5), for three days at a dose of 40,000 IU per day. Then, on the fourth to seventh days, two to three burr holes were perforated per cerebral hemisphere under local anesthesia. Clinical conditions of patients were examined and indexed for six months after treatment completion, and changes of cerebrovascular neovascularization before and after treatment were compared.

Patient 1 was a moyamoya syndrome patient (unilateral+ no moyamoya blood vessel) with right hemiplegia and total aphasia. Patient 2 was a moyamoya syndrome patient (unilateral+moyamoya blood vessel) with right hemiplegia and total aphasia. Patient 3 was a moyamoya patient (bilateral+ moyamoya blood vessel) with a consciousness disorder. Patient 4 was a moyamoya syndrome patient (bilateral+no moyamoya blood vessel) with right hemiplegia. Patient 5 was a moyamoya patient (bilateral+moyamoya blood vessel) with right hemiplegia. Patient 6 was a moyamoya syndrome patient (unilateral+no moyamoya blood vessel) with right hemiplegia. Patient 7 was a moyamoya disease patient (bilateral+moyamoya blood vessel) with left hemiplegia. Patient 8 was a moyamoya syndrome patient (bilateral+no moyamoya blood vessel) with right hemiplegia. Patient 9 was a moyamoya disease patient (bilateral+ moyamoya blood vessel) with right hemiplegia. Patient 10 was a moyamoya syndrome patient (unilateral+no moyamoya blood vessel) with transient left hemiplegia.

EXAMPLE 1-2

Analysis of Neurological and Functional Conditions of Patients

An NIH stroke scale, a modified barthel index and a modified Rankin scale were respectively measured for patients 1 to 4 who had the multiple burr-hole operation, and changes of average values thereof were analyzed over time (refer to FIGS. 3 to 5).

An NIH stroke scale, a modified barthel index and a modified Rankin scale were measured for patients 5 to 10 who had the multiple burr-hole operation, and changes of average values thereof were analyzed over time (refer to FIG. 6).

The NIH stroke scale is a tool used to quantify neurological symptoms by giving a score between 0 and 34. A score closer to 0 indicates a better prognosis. The modified barthel index has a score of between 0 and 100. Based on activities of daily living, a higher score indicates a good prognosis. The modified Rankin scale has a score of between 0 and 6. A score of 6 indicates death, and a score of 1 indicates that all usual activities are able to be carried out, despite some symptoms.

FIG. 3 is a graph illustrating a change of an average value of NIH stroke scales of patients 1 to 4 over time. FIG. 4 is a graph illustrating a change of an average value of modified barthel indexes of patients 1 to 4 over time. FIG. 5 is a graph illustrating a change of an average value of modified Rankin scales of patients 1 to 4 over time.

As illustrated in FIGS. 3 to 5, it is understood that overall function conditions of all patients became worse on the seventh day from the time of admission and then recovered.

FIG. 6 is a graph illustrating changes of an average value of NIH stroke scales, an average value of modified barthel indexes, and an average value of modified Rankin scales of patients 5 to 10 over time. The patients had lower levels of stroke than patients 1 to 4. Like patients 1 to 4 having a high level of stroke, all of the patients having a low level of stroke showed function recovery.

In addition, postoperative complications were not observed in any patients (patients 1 to 10) and all patients showed function recovery after six months.

Based on the result, in the multiple burr-hole operation, when the composition according to the invention was used for aiding the multiple burr-hole operation for treatment of acute cerebral infarction caused by atherosclerotic ischemic stroke and moyamoya disease, it can be seen that a success rate of the treatment increased and the combination therapy was very safe.

EXAMPLE 1-3

Imaging and Analysis Cerebrovascular Images of Patients

Before the multiple burr-hole operation and six months after the operation, cerebrovascular images of each of the patients 1 to 10 were captured, compared and analyzed. FIGS. 7 to 16 are pictures showing cerebrovascular images of patients 1 to 10 captured before and after the multiple burr-hole operation using the composition for aiding the multiple burr-hole operation for treatment of acute cerebral infarction caused by atherosclerotic ischemic stroke and moyamoya disease.

Patient 1 had three holes, the first hole was drilled into only the cranium, the second hole was drilled up to the dura mater, and the third hole was drilled up to the pia mater. When only the cranium was perforated, neovascularization was not produced. When the hole was drilled up to the dura mater or deeper, neovascularization was produced. Therefore, it is understood that moyamoya disease was cured. As a result, it was verified that neovascularization is produced when the dura mater, which is an anatomically relatively rigid intra- or extra-cranial barrier, is sufficiently destroyed in the operation. All patients other than patient 1 were drilled up to the dura mater. In patients 1, 4, 6, 8, and 10, it was verified that neovascularization was produced in patients having no moyamoya blood vessel. It was also verified that neovascularization inducement may be used for strokes caused by arteriosclerotic obstructive artery diseases in addition to strokes caused by moyamoya disease.

Patients 6 and 8 were aged 70 years and older with cerebral arteriosclerotic obstructive artery diseases and a mild perfusion disorder, and a blood vessel pathway from the exterior cranium to the interior cranium was produced in both patients after six months.

Cerebral neovascularization was produced in patients 6, 8, and 10 without neurological deterioration.

As a result, according to the method of the invention, combination therapy was performed on adults aged 20 years and older with acute ischemic stroke [6 females, 10 subjects in total, an average age was 50.5±17.4 (in the range of 22 to 75)], and side effects caused by the treatment were not reported in any patients. Under current conditions in which there is no specific medication for acute phase cerebral infarction patients other than a blood vessel recanalization method, it is understood that the method may be a very safe method that can be performed on acute phase patients with unstable clinical conditions. In addition, in terms of effectiveness, a stable blood vessel pathway from the exterior cranium was produced in all 15 operated hemispheres and thus the method showed a 100% success rate of neovascularization regeneration. Furthermore, in terms of subjects, since 5 patients were moyamoya disease patients out of 10 patients and the remaining 5 patients were arteriosclerotic obstructive artery disease patients, the method was also effective in patients with cerebral vascular occlusion caused by arteriosclerosis. In terms of clinical trials, the combination therapy showed outstanding effectiveness and safety, and all participating patients showed function recovery according to scales measured by various methods.

EXAMPLE 2

Neovascularization in an Animal Model

EXAMPLE 2-1

Preparation of an Appropriate Animal Model

In order to verify effects occurring in the human body of the composition according to the invention on animals, various animal models were prepared. Appropriate animal models were prepared to perform the same method as the method performed on the human body as much as possible. Male Sprague-Dawley rats of 290 to 340 g were inhalation-anesthetized with 3.5% isoflurane, and then a common carotid artery (CCA), an external carotid artery (ECA), and an internal carotid artery (ICA) were exposed. During surgical procedures, a rectal temperature was maintained at 37° C. through an electronic temperature controller connected to a heating pad. Left blood vessels of rat collum were exposed by the same method. In group 1, one-side internal carotid artery was tied up, and an opposite-side carotid artery was tied up. In group 2, a unilateral vertebral artery of rats to which a method of group 1 was applied was blocked using an electric coagulator. In group 3, an opposite-side vertebral artery of rats to which a method of group 2 was applied was also blocked using the electric coagulator. In group 4, permanent unilateral middle cerebral artery occlusion was performed using a nylon thread in a blood vessel lumen.

Since severe cerebral artery occlusion killed almost all rats (a mortality rate of 86% in rat groups 1 to 3), it was difficult to use as a long-term neovascularization model. In addition, a model of group 4 showed a mortality rate of 64%. Therefore, a model with a lower level of cerebral infarction was considered to be appropriate and thus a 90 minutes occlusion-reperfusion middle cerebral artery model was used.

EXAMPLE 2-2

Effects of Combination Therapy (EPO and Burrhole Operation) in an Animal Model

Male Sprague-Dawley rats of 290 to 340 g were inhalation-anesthetized with 3.5% isoflurane, and then a CCA, an ECA, and an ICA were exposed. A 4-0 monofilament nylon thread (3 cm) was inserted into the ICA through the ECA, and advanced until a middle cerebral artery (MCA) was blocked, and thus ischemic brain damage was induced. Ninety minutes After MCA occlusion (MCAo), inhalation-anesthesia was performed again, the thread was disruptiond, and reperfusion was performed. During surgical procedures, a rectal temperature was maintained at 37° C. through an electronic temperature controller connected to a heating pad. In order to achieve purposes of the experiment, rats were divided into three groups and results thereof were compared. In group 1 (control: t-MCAO+no burr hole), an animal model was prepared according to the above method, and natural progress was observed. In group 2 (t-MCAO+burr hole), a cerebral infarction animal model was prepared, and then a minimally invasive operation was performed on the third day. In group 3 (t-MCAO+EPO+burr hole), a cerebral infarction animal model was prepared, as preconditioning for cerebrovascular neovascularization, EPO was administered in the abdominal cavity for three days at a dose of 5000 U/kg/day, and then a minimally invasive operation was performed on the third day. In the minimally invasive operation, rats were inhalation-anesthetized, and then a hole having a diameter of 4 mm was made in a temporal bone using a drill in FIG. 17. After the operation was completed, an operation region was sutured using a 5-0 nylon thread.

Results of observation for 3 to 4 months in total are shown in Table 1. As shown in Table 1, a mortality rate was 63.6% (7/11) in group 1, 31.6% (6/19) in group 2, and 5.3% (1/18) in group 3. There was a statistically significant difference in the mortality rate (p=0.003). In addition, a volume of cerebral infarction for three months was 348±42 mm$^3$ in group 1, 298±58 mm$^3$ in group 2, and 280±67 mm$^3$ in group 3. Two weeks later, the modified neurological severity score (mNSS), which indicates functions on a scale of 0 to 28 (a higher score indicates a bad function), was observed. The result showed a statistically significant difference (P <0.001) such that 19.0±1.9 in group 1, 11.1±3.9 in group 2, and 10.8±3.8 in group 3. In terms of neovascularization regeneration for three months as a final goal, there was a statistically significant difference (P=0.047) of 0/4 (0%) in group 1, 3/7 (42.9%) in group 2, and 6/8 (75.0%) in group 3.

TABLE 1

| | Mortality rate | Cerebral infarction volume | mNSS | Neo-vascularization regeneration |
|---|---|---|---|---|
| Group 1 (t-MCAO + no burr hole) | 63.6% | 348 ± 42 mm$^3$ | 19.0 ± 1.9 | 0% |
| Group 2 (t-MCAO + burr hole) | 31.6% | 298 ± 58 mm$^3$ | 11.1 ± 3.9 | 42.9% |
| Group 3 (t-MCAO + EPO + burr hole) | 5.3% | 280 ± 67 mm$^3$ | 10.8 ± 3.8 | 75.0% |

Methylene blue dye was injected into the ECA to observe a blood vessel connection into the cranium from the scalp. Pictures in FIG. 23 show that there is no region stained with methylene blue in a right hemisphere of rats in group 1, a region was weakly stained in group 2, and a region was strongly stained in group 3.

As a result, since it was observed that a new blood vessel was not produced in necrotic tissues, a cerebral infarction model having a lower level of cerebral infarction than the present model may be preferable. In addition, since there was a significant difference of prognosis based on whether the operation was performed, a minimal burrhole operation may be useful to compare medication effects and may show effective neovascularization regeneration eventually. Accordingly, the following experiments were additionally performed.

EXAMPLE 2-3

Effects of Combination Therapy (EPO, Burrhole Operation, and VEGF) in an Animal Model Based on the above example results, in order to decrease a level of cerebral infarction in this experiment, a reperfusion time was reduced, a size of a hole was reduced to 2 mm, and a vascular endothelial growth factor (VEGF) was added as pre- and post-conditioning for neovascularization regeneration and used in addition to EPO. Male Sprague-Dawley rats of 290 to 340 g were used to prepare an animal model, and only two rats were used to prepare a model in order to determine whether neovascularization regeneration occurred. Similarly to the above method, a cerebral artery 60 minute occlusion-reperfusion method was used to induce cerebral infarction, and then EPO was administered in the abdominal cavity for three days at a dose of 5000 U/kg/day. An rh-VEGF-A165 was administered in the abdominal cavity at a dose of 50 ng/kg/min using an injection pump on the third, sixth, and ninth days after the operation.

As a result of observation for three months in total, a mortality rate was 0% (0/2), a volume of cerebral infarction was 292±15 mm$^3$, a modified neurological severity score (mNSS, indicates functions of rats on a scale of 0 to 28 and a higher score indicates a bad function) on the seventh day was 10.7±3.2. Methylene blue dye was injected into the ECA to observe a blood vessel connection toward inside cranium from the scalp. Pictures in FIG. 24 show that cerebral regions of two rats were strongly stained and neovascularization was successfully produced.

According to human and animal experiment results, it is understood that the composition for treatment of ischemic cerebrovascular diseases according to the invention facilitates blood vessel formation environments in the patient's brain. In addition, when the composition is used along with the easy and safe operation for ischemic blood vessel related diseases such as the multiple burr-hole operation in an acute phase vascular occlusion (within one week after onset of symptoms), it is understood that prognosis of a living body with tissue ischemic symptoms was improved through neovascularization. Furthermore, according to human and animal experiment results, it is understood that neovascularization may be enhanced when EPO, which is contained in the composition, is administered before the operation for eliminating an anatomical barrier to produce a blood vessel. The animal experiment showed that such neovascularization may be further enhanced when the rhVEGF-A165 protein is used after the operation.

With regard to treatment for acute cerebral infarction, substances did not reach the cerebrum due to cerebral vascular occlusion and did not show effectiveness thereof. However, in the method according to the invention, a pathway enabling various substances to reach the cerebrum is regenerated and the pathway is expected to be used as various drug delivery methods later.

The above description of the invention is only exemplary, and it will be understood by those skilled in the art that various modifications can be made without departing from the scope of the present invention and without changing essential features. Therefore, the above-described embodiments should be considered in a descriptive sense only and not for purposes of limitation.

The composition according to the invention may be effectively and widely used to treat ischemic vascular diseases including ischemic cerebrovascular diseases, ischemic cardiovascular diseases, and ischemic peripheral vascular diseases.

The invention claimed is:

1. A method for treatment of cerebral ischemic vascular diseases comprising, in this order:
    a) administration of a composition comprising erythropoietin (EPO) active ingredient to a patient about to undergo a burrhole operation for cerebral ischemic vascular diseases, and
    b) performing a burrhole operation, wherein the burrhole is drilled up to dura mater.

2. The method of claim 1, wherein the composition is administered to a patient with an acute phase vascular occlusion.

3. A method for treatment of cerebral ischemic vascular diseases consisting of, in this order:
   a) administering a composition comprising erythropoietin (EPO) as an active ingredient to a patient about to undergo a burrhole operation for cerebral ischemic vascular diseases, and
   b) performing a burrhole operation, wherein the burrhole is drilled up to dura mater.

4. The method of claim 3, wherein the composition is administered to a patient: with an acute phase vascular occlusion.

\* \* \* \* \*